Figure 8:
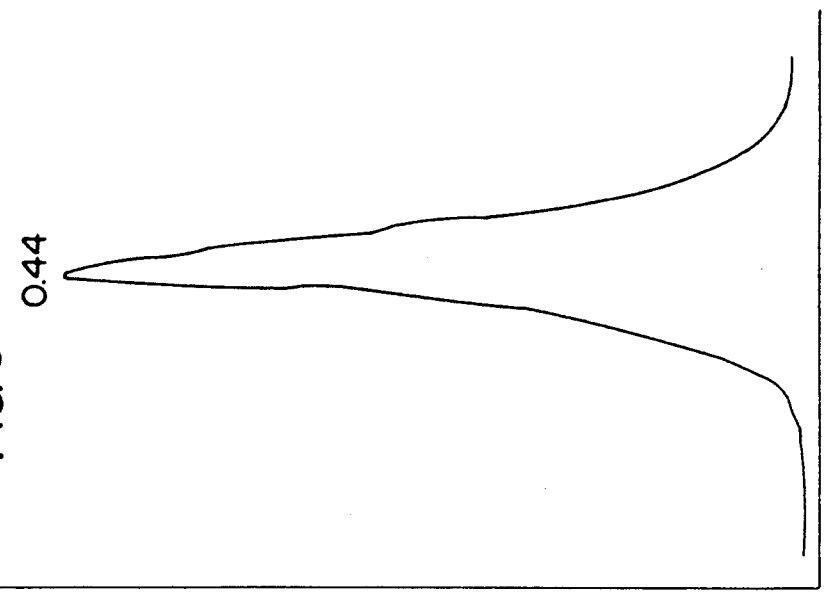

United States Patent [19]

Demoute et al.

[11] Patent Number: 5,024,828

[45] Date of Patent: Jun. 18, 1991

[54] NOVEL RADIOACTIVE PYRETHRINOIDS AND USE THEREOF

[75] Inventors: Jean-Pierre Demoute, Montreuil-sous-Bois; Gaëtan Touyer; Michel Mouren, both of Paris, all of France

[73] Assignee: Roussel Uclaf, Paris, France

[21] Appl. No.: 7,648

[22] Filed: Jan. 28, 1987

[30] Foreign Application Priority Data

Jan. 29, 1986 [FR] France .................. 86 01220

[51] Int. Cl.⁵ .............................. A61K 43/00
[52] U.S. Cl. .................... 424/1.1; 424/88; 436/504; 436/545; 436/547; 436/804; 530/350; 530/380; 530/387; 530/362; 530/363; 530/403; 530/807; 558/407; 548/343; 548/344
[58] Field of Search ............... 424/1.1, 88; 436/504, 436/518, 545, 547, 804; 530/807; 558/407

[56] References Cited

U.S. PATENT DOCUMENTS

| | | | |
|---|---|---|---|
| 4,136,159 | 1/1979 | Stone | 544/257 |
| 4,302,438 | 11/1981 | Zeeh | 436/807 |
| 4,544,510 | 10/1985 | van Berkel et al. | 558/407 |

OTHER PUBLICATIONS

Wing et al., J. Agric. Food Chem., 26(6), pp. 1328–1332 (1978).

*Primary Examiner*—Sam Rosen
*Attorney, Agent, or Firm*—Bierman and Muserlian

[57] ABSTRACT

Novel isomers or mixtures of isomers of radioactive pyrethrinoids marked with iodine of the formula

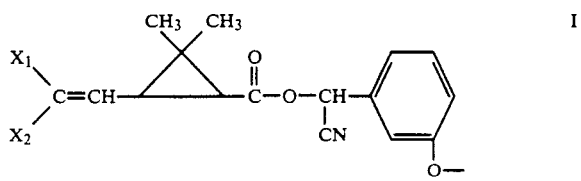

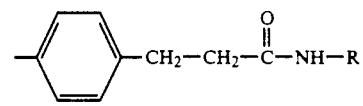

wherein $X_1$ is selected from the group consisting of halogen and $-CF_3$, $X_2$ is a halogen, R is the residue of an amino acid of the formula $R-NH_2$ or a derivative thereof containing an iodine acceptor group and marked with iodine$^{125}$ or iodine$^{131}$, process for their preparation and intermediates and their use in radioimmunological determination.

10 Claims, 4 Drawing Sheets

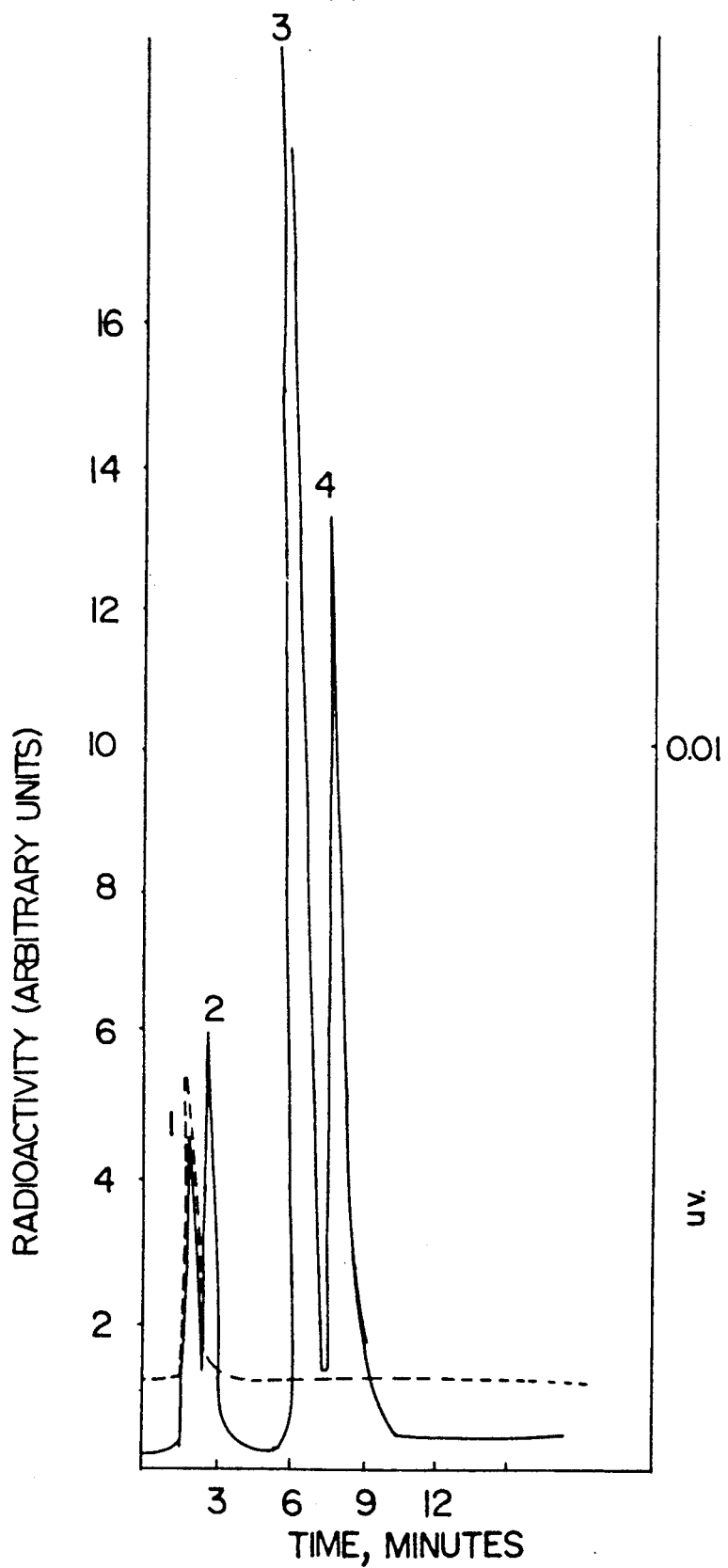

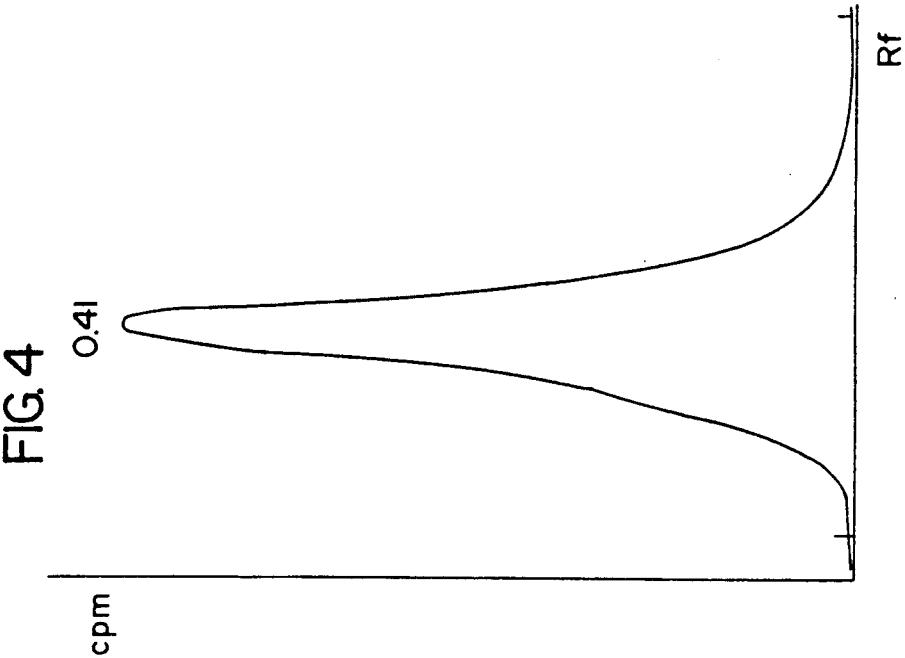
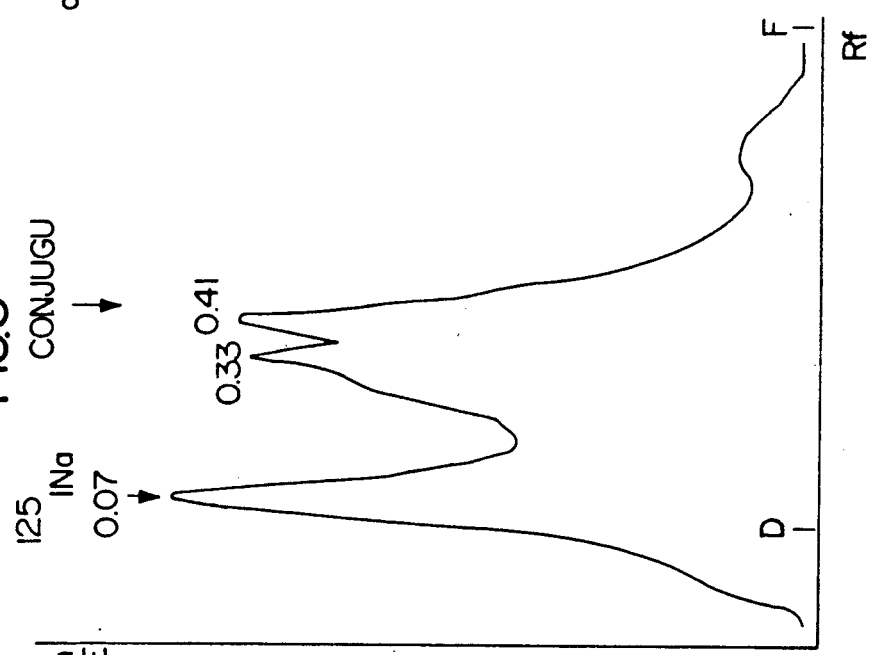
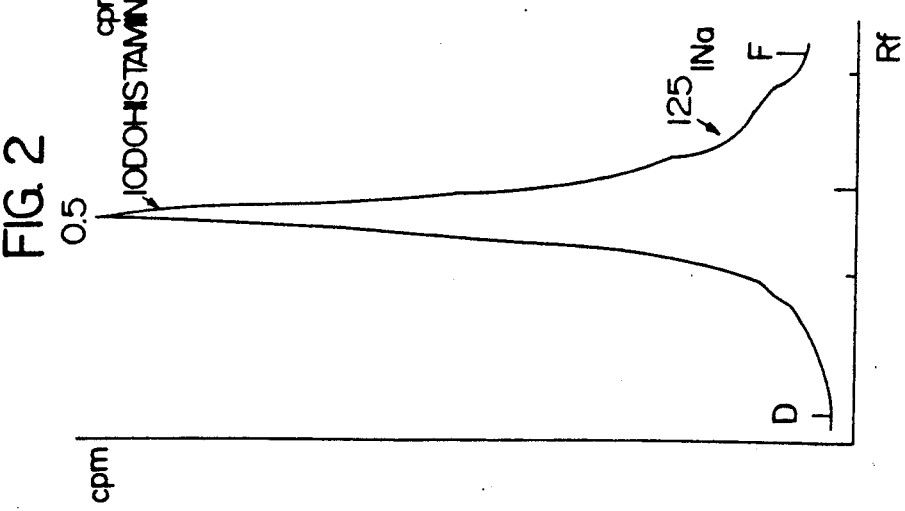

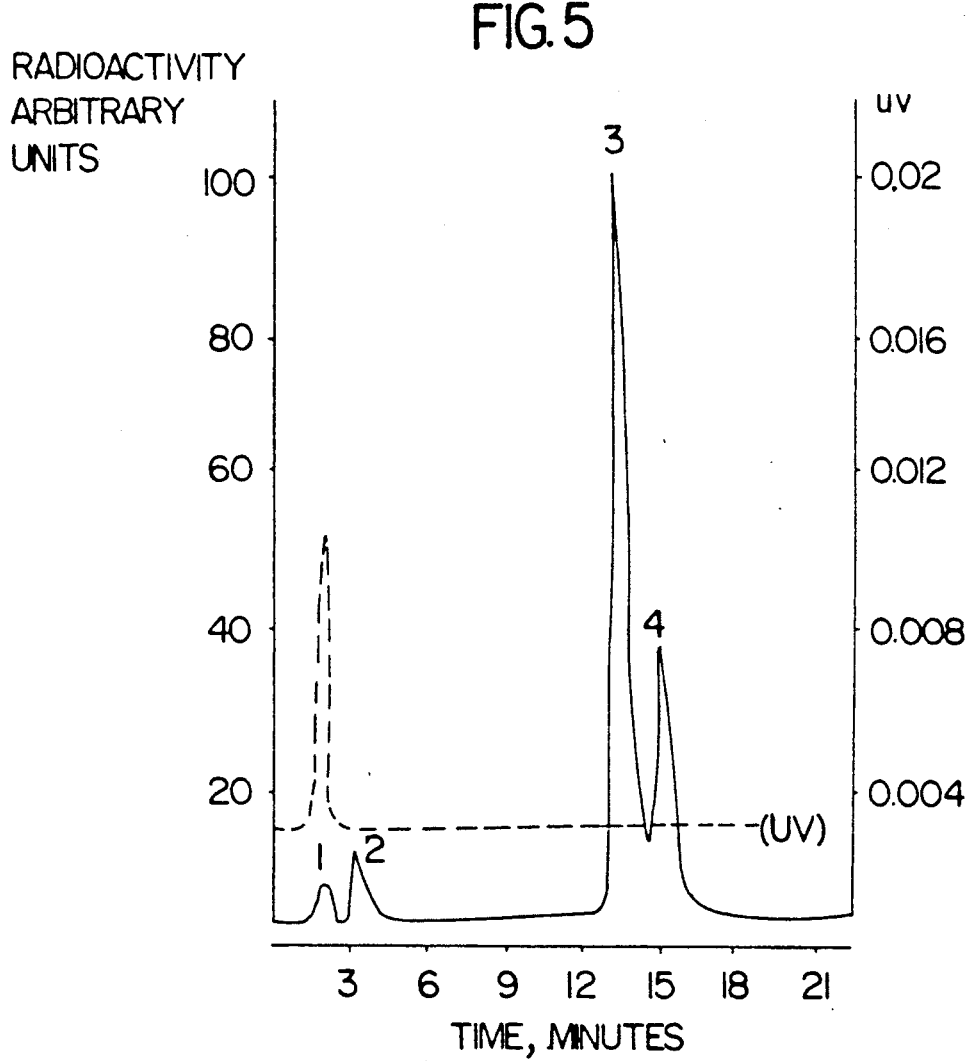

NOVEL RADIOACTIVE PYRETHRINOIDS AND USE THEREOF

STATE OF THE ART

U.S. Pat. No. 4,136,159 is related to the field of technology.

OBJECTS OF THE INVENTION

It is an object of the invention to provide the novel radioactive pyrethrinoids of formula I and a process and novel intermediates for their preparation.

It is another object of the invention to provide novel antigens and novel methods of radioimmunological determinations.

These and other objects and advantages of the invention will become obvious from the following detailed description.

THE INVENTION

The novel compounds of the invention are isomers or mixtures of isomers of radioactive pyrethrinoids marked with iodine of the formula

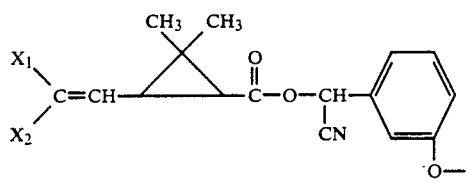

I

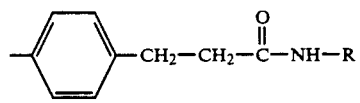

wherein $X_1$ is selected from the group consisting of halogen and $-CF_3$, $X_2$ is a halogen, R is the residue of an amino acid of the formula $R-NH_2$ or a derivative thereof containing an iodine acceptor group and marked with iodine[125] or iodine[131]. Mixtures of isomers are all possible isomeric mixtures including racemates.

Examples of $X_1$ and $X_2$ are fluorine, chlorine, bromine and iodine. Examples of $R-NH_2$ are histidine, tyrosine, histidinol, histamine, tyramine and methyl tyrosinate marked with iodine[125] or [131].

A preferred group of compounds of formula I are those wherein $X_1$ is $-CF_3$, bromine or chlorine, those wherein $X_2$ is chlorine or bromine and especially those wherein $X_1$ and $X_2$ are both bromine.

A preferred compound of the invention is 1R-[1αS, 2α-]4-[3-(cyano-[3-(2,2-dibromoethenyl)-2,2-dimethyl-cyclopropylcarbonyloxy]-methyl)-phenoxy]-benzene-N-[2-(2-iodo[125]I 4-1H-imidazolyl)-ethyl]-propanamide of the formula

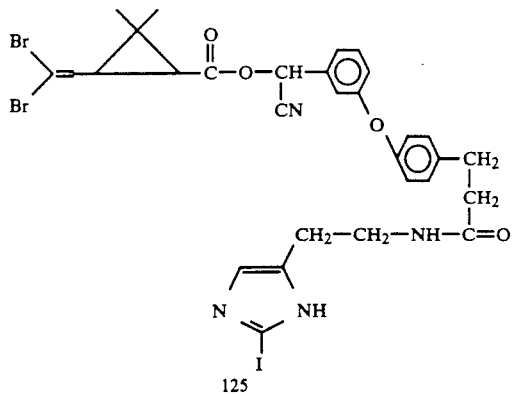

The novel process of the invention for the preparation of the compounds of formula I comprises reacting a compound of the formula

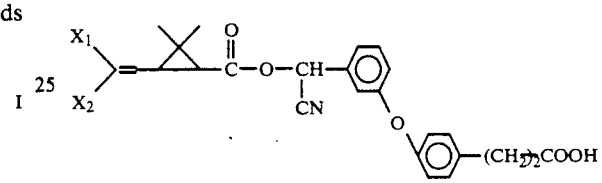

II wherein $X_1$ and $X_2$ have the above definitions in any isomeric form or mixtures thereof with a reagent capable of fixing an activator group of the carbonyl to obtain a compound of the formula

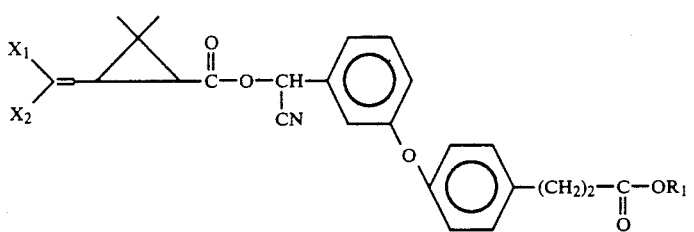

III wherein $R_1$ is the activator group of the carbonyl group and reacting the latter with an amino acid of the formula $R-NH_2$ with an iodine acceptor group marked with iodine[125] or [131] or a derivative thereof to obtain the corresponding compound of formula I which may be purified by physical means.

In a preferred mode of the process of the invention, the amino acid iodine acceptor or the amino acid derivative is selected from the group consisting of histidine, tyrosine, histidinol, histamine, tyramine and methyl tyrosinate: an activator group of the carbonyl function is fixed on the acid function by reacting an alkyl haloformate wherein the alkyl has 1 to 6 carbon atoms in the presence of a tertiary base in an anhydrous medium and under inert atmosphere. The preferred alkyl haloformate is isobutyl chloroformate and the operation is carried out in the presence of tri-n-butyl amine.

The amino acid or its derivative which is reacted with the product of formula III in which $R_1$ is an activator group of the carbonyl function is histamine marked with iodine[125] or [131] or a derivative and the operation is carried out under inert atmosphere.

The products of formula I are useful in the study of and in the radioimmunological determination of the corresponding esters of α-cyano-3-phenoxy-benzyl alcohol (product B) in biological fluids of man and animals. 1R-[1αS, 2α]-4-[3-(cyano-[3-(2,2-dibromoethenyl)-2,2-dimethyl-cyclopropylcarbonyloxy]-methyl]-phenoxy]-benzene-N-[2-(2-iodo125I-4-1H-imidazolyl)-methyl]-propanamide (product A) is useful in the study of and in the radioimmunological determination of deltamethrine (product B₁) in biological fluids of man and animals.

The novel intermediate products of the invention are the compounds of the formula

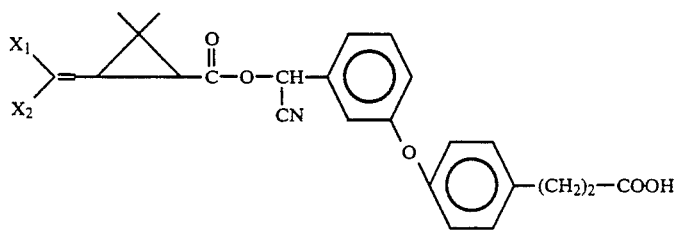

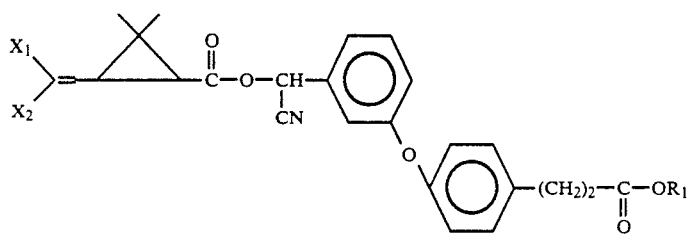

wherein $X_1$, $X_2$ and $R_1$ have the above definitions in any one of their isomeric forms and mixtures of the isomers. Among the preferred products of formula III are those wherein $R_1$ is

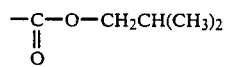

and $X_1$ and $X_2$ are bromine of the formula

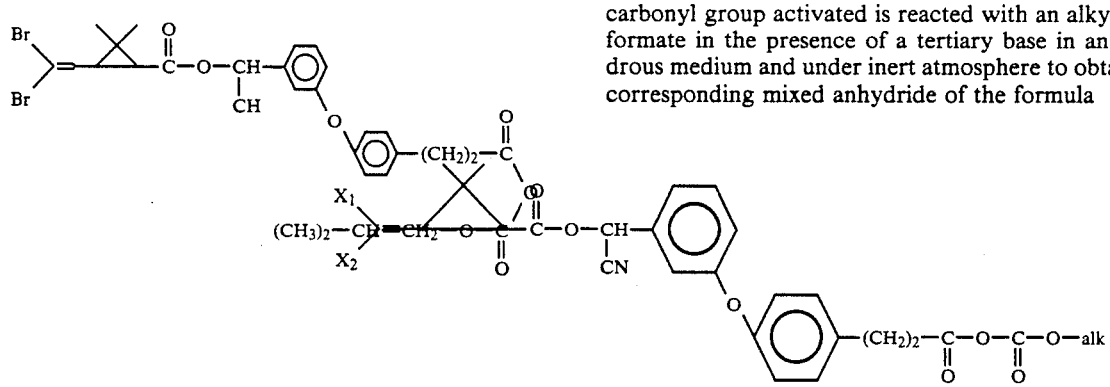

The products of formula II a starting products also useful for the preparation of antigens which are necessary for radioimmunological determinations of the product B. The use of the products of formula II for the preparation of antigens is also the subject of the present invention and the products of formula II or an activated form are conjugated with bovine serum albumin (B.S.A.) or with another or with another immunogenic protein such as human serum albumin, porcine or bovine, thyroglobulin, tetanus anatoxine, diphtheria anatoxine, egg-albumin, hemocyanin of Patelle (KLH) or gamma globulins to obtain the sought antigens.

In a preferred mode of this process, a product of the formula

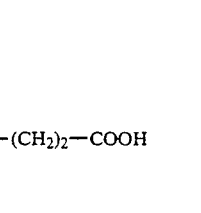

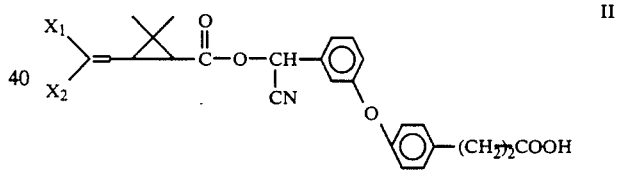

wherein $X_1$ and $X_2$ have the above definitions with the carbonyl group activated is reacted with an alkyl haloformate in the presence of a tertiary base in an anhydrous medium and under inert atmosphere to obtain the corresponding mixed anhydride of the formula

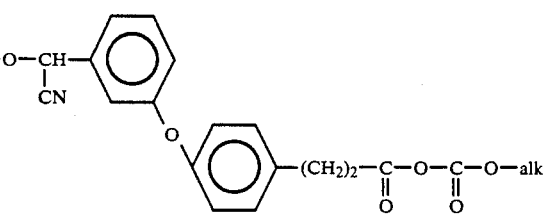

wherein alk has the above definition and conjugating the latter with bovine serum albumin (B.S.A.) or with another immunogenic protein to obtain the sought antigen. Preferably, the alkyl haloformate is isobutyl chloroformate and the operation is carried out in the presence of tri-n-butyl amine and the mixed anhydride of formula III₁ is reacted with bovine serum albumin (B.S.A.) or another immunogenic protein previously dissolved in a water-dioxane mixture.

Starting from the product of the formula

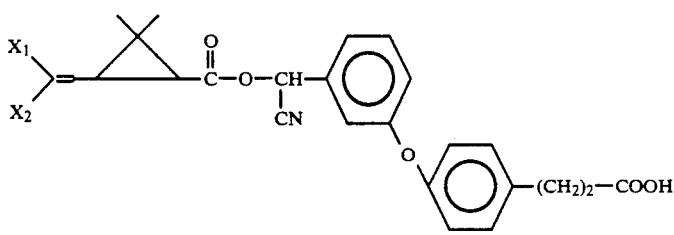

one obtains the novel antigens of formulae

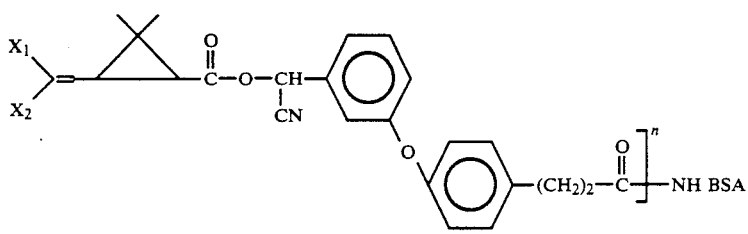

where n is 10 to 30 and

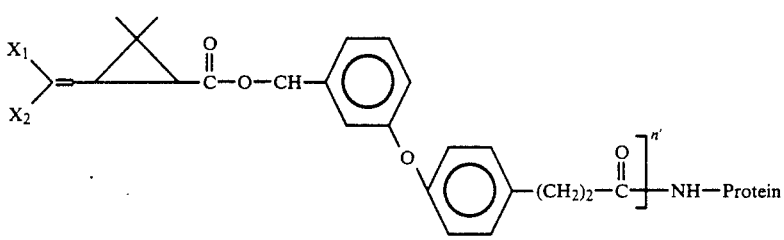

wherein n' is 10 to 100. The antigens are useful in the preparation of antibodies by injection into animals in the presence of adjuvants.

The products of formula 1 can be used during the studies and during the radioimmunological determination of the products B and in particular the product A for deltamethrin. In these studies, the products of formula I enable an easy specific determination of quantities of the order of a few tens of picograms of product B, without being obliged to have recourse to chromatographic isolation and purification methods, before proceeding to the proper determination according to the conventional radioimmunological methods such as those described by: S. A. BERGSON and R. S. YALOW, HORMONE 4, p. 557 (1964) and G. E. ABRAHAM J. of CHEM. ENDOCRINAL METAB., 29, p. 866 (1969).

Referring now to the Drawings

FIG. 1 is a HPLC profile of the iodized conjugate under chromatography conditions as follows:

Column Zorbax Golden Sil, 3 μm; mobile phase; CHCl$_3$ MeOH (98/2,v/v); flow; 1 ml/min.; pressure: 800 PSI; sample 25 μl; detection. Radioactivity Beckman model 170, μv..uvicord LKB 276 nm 0.02. Detection of the radioactivity of the Beckman model 170 for peaks 1 to 4 was a retention time in minutes of 2.44, 3.17, 6.93 and 8.57 respectively which indicated a percent of radioactivity of 5.34, 8.00, 63.46 and 22.98 respectively.

FIGS. 2, 3 and 4 are radiochromatograms of A$^{125}$ iodohistamine (medium B); B: radioactive conjugate (medium C); C: peak 3 purified conjugate (solution D); plates of silica Merck 60F 254; solvents, A: EtOH—H$_2$O—NH$_4$OH (77/18/5); B and C: cyclohexane-EtOH-triethylamine (77/30/1). Plate reader: Berthold LB 2832.

FIG. 5 is a HPLC profile of the iodized conjugate. Chromatography conditions: column Zorbax Sil, 3 μm; mobile phase: CHCl$_3$/MeOH 97/3 (v/v); flow: 1 ml/min.; pressure: 800 PSI; sample 70 μl; detection: radioactivity Berthold sook, μv uvicords LKB 276 nm 0.02.

Figure 7:
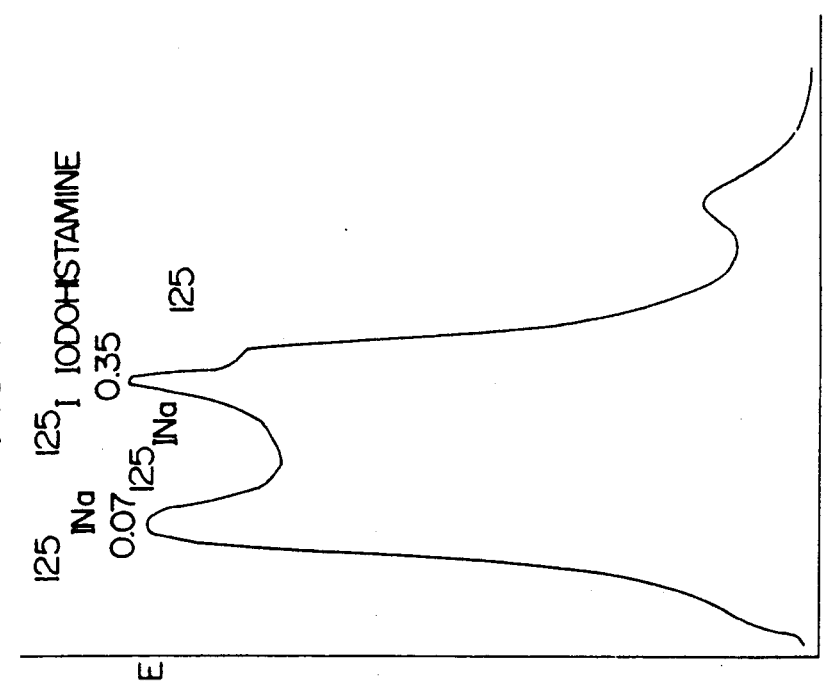
Figure 6:
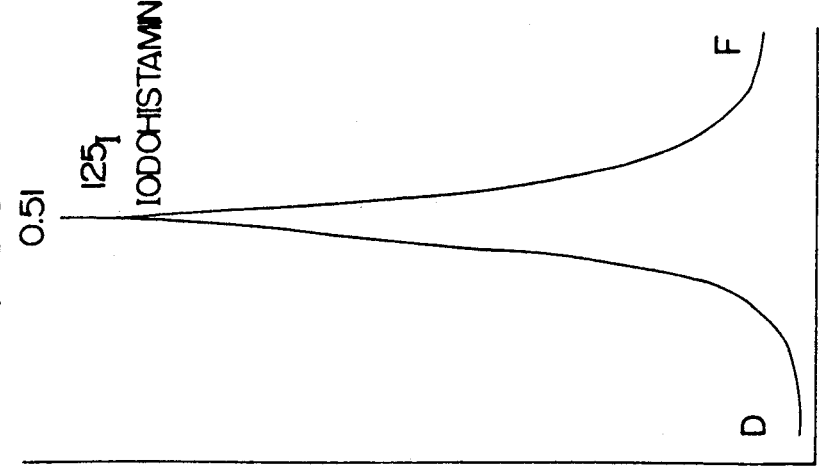

FIGS. 6, 7 and 8 are radiochromotographs of A$^{125}$ iodohistamine (medium B); B: radioactive conjugate medium (medium C); C: peak 3 (solution D); plates of silica Merck 60F 254; solvents, A: EtOH—H$_2$O—NH$_4$OH (77/18/5); B and C: cyclohexane-EtOH-triethylamine (70/30/1). Plate reader: Berthold 1b 2832.

In the following examples there are described several preferred embodiments to illustrate the invention. However, it should be understood that the invention is not intended to be limited to the specific embodiments.

EXAMPLE 1

1R-1-α(R),
2-α]4-[3-(cyano[(2-(2,2-dibromo-ethenyl)-3,3-dimethylyclopropylcarbonyloxy]-methyl)-phenoxy]-benzene propanoic acid STEP A:
4-[3-1,3-dioxolan-2-yl)-phenoxy]-benzaldehyde A mixture of 12.05 g of p-hydroxybenzaldehyde, 30 ml of pyridine and 5.5 g of sodium methylate was heated to distill off 4 ml of pyridine and then 2.5 g of cuprous chloride and 38 g of 2-(m-bromophenyl)-1,3-dioxolane were added. The mixture was heated with strong stirring at 200° C. (external temperature), while still distilling the pyridine, and maintained at 200° C. (external temperature) for 5 hours. After cooling, the residue was taken up in methylene chloride, washed with an N aqueous solution of hydrochloric acid, then with water and the organic phase was dried and concentrated to dryness by distillation under reduced pressure. The residue was chromatographed over silica and eluted with a hexane-ethyl acetate mixture (6/4) to obtain 18.28 g of the 4-[3-(1,3-dioxolan-2-yl)-phenoxy]-benzaldehyde.

IR Spectrum (chloroform):

| | |
|---|---|
| 2,830 cm$^{-1}$ | |
| 2,738 cm$^{-1}$ | aldehyde |
| 1,696 cm$^{-1}$ | C=O |
| 1,598 cm$^{-1}$ | |
| 1,580 cm$^{-1}$ | aromatics |
| 1,500 cm$^{-1}$ | |
| 1,240 cm$^{-1}$ | |
| 1,097 cm$^{-1}$ | |
| 1,071 cm$^{-1}$ | |
| 1,076 cm$^{-1}$ | |
| 833 cm$^{-1}$ | |

NMR Spectrum, (CDCl$_3$)

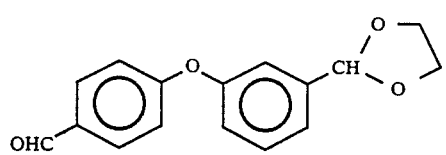

STEP B: 2-[3-(4-[ΔE (1,1-dimethylethoxy)-1-oxopropenyl]-phenoxy)-phenyl]-1,3-dioxolane A mixture of 137 ml of tetrahydrofuran and 13.72 g of lithium bromide was cooled to −30° C. and 11.94 ml of diisopropylamine were added all at once. Then, a mixture of 10 g of 4-[3-(1,3-dioxolan-2-yl)-phenoxy]-benzaldehyde, 200 ml of tetrahydrofuran and 10.09 g of 0,0-diethyl-tert-butyloxcarbonylmethyl phosphonate was added and the mixture stirred for 16 hours at −15° C. The reaction mixture was poured into water and extracted with ethyl ether. The extracts were evaporated to dryness by distillation under reduced pressure and the residue was chromatographed over silica and eluted with a hexane and ethyl acetate mixture (8/2) to obtain 13.48 g of 2-[3-(4-ΔE (1,1-dimethylethoxy)-1-oxopropenyl]-phenoxy)-phenyl]-1,3-dioxolane.

IR Spectrum (chloroform):

| | |
|---|---|
| 1,700 cm$^{-1}$ | C=O |
| 1,634 cm$^{-1}$ | C=C |
| 1,602 cm$^{-1}$ | |
| 1,590 cm$^{-1}$ | |
| 1,506 cm$^{-1}$ | aromatics |
| 1,487 cm$^{-1}$ | |
| 982 cm$^{-1}$ | —CH=CH— |

NMR Spectrum, (CDCl$_3$)

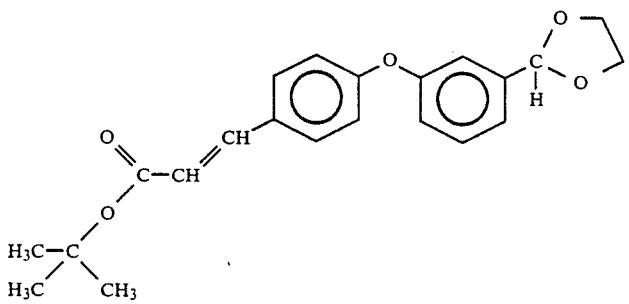

STEP C: Mixture of: dimethoxymethyl 3-(4-[ΔE-(1,1-dimethyl-ethoxy)-1-oxopropyl)]-phenoxy)-benzene and methoxymethyl 3-(4-[ΔE-(1,1-dimethylethoxy)-1-oxopropyl]-phenoxy)-benzene 1.5 g of palladium hydroxide deposited on barium sulfate (5% palladium) were mixed with 10 ml of methanol and a solution of 12 g of 2-[3-(4-[ΔE (1,1-dimethylethoxy)-1-oxopropenyl]-phenoxy)-phenyl]-1,3-dioxolane was introduced. The mixture was stirred under hydrogen for 75 minutes to absorb 717 ml of hydrogen and after filtering, the filtrate was evaporated to dryness under reduced pressure. The residue was chromatographed over silica and eluted with a mixture of hexane and ethyl acetate (9/1) to obtain 7.16 g of a 50/50 mixture of the above two compounds.

IR Spectrum (chloroform):

| | |
|---|---|
| 1,605 cm$^{-1}$ | |
| 1,586 cm$^{-1}$ | |
| 1,506 cm$^{-1}$ | aromatics |
| 1,483 cm$^{-1}$ | |
| 1,250 cm$^{-1}$ | |
| | 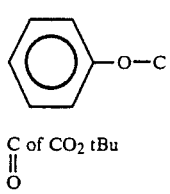 |
| 1,720 cm$^{-1}$ | C of CO$_2$ tBu |

-continued

| | |
|---|---|
| 1,369 cm$^{-1}$ | methyl |
| 1,147 cm$^{-1}$ | C—O—C |

NMR Spectrum, (CDCl$_3$):

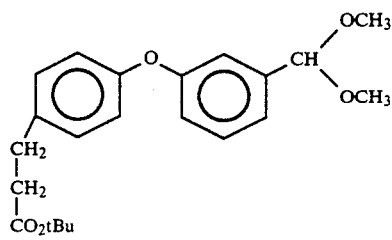

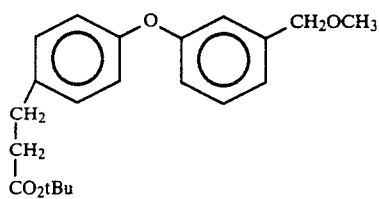

STEP D:
3-[4-(1,1-dimethylethoxy)-1-oxopropyl]-phenoxy]-benzaldehyde 6 g of the mixture of compounds of Step C, 30 ml of acetone and 24 ml of N aqueous solution of hydrochloric acid were mixed together and 42 ml of acetone were added to obtain a single phase. The mixture was stirred for 2 hours and 30 minutes at 20° C. and was poured into water. The mixture was extracted with methylene chloride and the extracts were evaporated to dryness under reduced pressure. The residue was chromatographed over silica and eluted with a mixture of hexane and ethyl and ethyl acetate (9/1) to obtain 2.74 g of 3-[4-[(1,1-dimethylethoxy)-1-oxopropyl]-phenoxy]-benzaldehyde.

IR Spectrum (chloroform):

| | | |
|---|---|---|
| 2,740 cm$^{-1}$ | } | C—H |
| 2,820 cm$^{-1}$ | | |
| 1,701 cm$^{-1}$ | | C=O |
| 1,720 cm$^{-1}$ | | C=O of CO$_2$ tBu |

NMR Spectrum:
1.45 ppm H of tertbutyl;
2.38 to 3.1 ppm H of CH$_2$;
6.9 to 7.65 ppm H aromatics;
10.01 ppm H of CHO.

STEP E:
cyano-[3-(4-[3-(1,1-dimethylethoxy)-3-oxopropyl-]-phenoxy)-benzyl [1R-(1-α(S), 3α)]3-(2,2-dibromoethenyl)-2,2-dimethylcyclopropane carboxylate and
cyano-[3-(4-[3-(1,1-dimethylethoxy)-3-oxopropyl]-phenoxy)-benzyl [1R-(1-α(R), 3α]3-(2,2-dibromoethenyl)-2,2-dimethylcyclopropane carboxylate 0.45 g of sodium cyanide, 0.0137 g of tetradecyl trimethyl ammonium bromide and 8.22 ml of water were mixed together and a mixture of 2.74 g of 3-[4-(1,1-dimethylethoxy)-1-oxopropyl]-phenoxy]-benzaldehyde of Step D, 0.0137 g of tetradecyl trimethyl ammonium bromide and 2.74 ml of toluene was introduced at 20° C. with strong stirring together with a mixture of 2.68 g of 1R, cis 3-(2,2-dibromoethenyl)-2,2-dimethylcyclopropane carboxylic acid chloride and 2.74 ml of toluene. After stirring for 3 hours at 20° C., an N aqueous solution of hydrochloric acid was added up to pH of 7, and the mixture was decanted. The organic phase was washed with water and the aqueous phase was extracted with toluene. The reunited toluene solutions were evaporated to dryness under reduced pressure and the residue was chromatographed over silica. Elution with a mixture of hexane and ethyl acetate (9/1) yielded 4.92 g of crude mixture of isomers (R) and (S) of the above compounds.

The crude mixture was chromatographed over silica and eluted with a mixture of hexane and isopropyl ether (7/3) to obtain 3 fractions:
a) 1.46 g of a fraction containing isomer R,
b) 2.64 g of a fraction containing a mixture of isomers R and S,
c) 0.395 g of a fraction containing isomer S.

Fraction b) was purified by chromatography over silica and elution with a mixture of hexane and isopropyl ether (7/3) to obtain 2 fraction
d) 0.67 g of a fraction containing isomer R
e) 1.66 g of a fraction containing isomer S IR Spectrum (chloroform):

| | isomer R | isomer S |
|---|---|---|
| ![structure] —C—O—CH with CN | 1,736 cm$^{-1}$ | 1,736 cm$^{-1}$ |
| ![structure] —O— with CH$_2$ | 1,603 cm$^{-1}$<br>1,591 cm$^{-1}$<br>1,506 cm$^{-1}$ | 1,603 cm$^{-1}$<br>1,591 cm$^{-1}$<br>1,506 cm$^{-1}$ |
| CH$_2$—CO$_2$tBu | 1,487 cm$^{-1}$ (max) | 1,487 cm$^{-1}$ (max) |
| C<br>‖<br>O | 1,722 cm$^{-1}$ | 1,722 cm$^{-1}$ |
| Me<br>C—O—C | 1,370 cm$^{-1}$<br>1,148 cm$^{-1}$ | 1,370 cm$^{-1}$<br>1,148 cm$^{-1}$ |

NMR Spectrum (CDCl$_3$)

| | isomer R | isomer S |
|---|---|---|
| hydrogens of paired methyls | 1.31 ppm | 1.2–1.25 ppm |
| hydrogen of tBu | 1.44 ppm | 1.42 ppm |
| hydrogens of cyclopropyl | 1.82 to 2.18 ppm | 1.75 to 2.2 ppm |
| hydrogens of CH$_2$ of the alkyl chain | 2.37 to 3.07 ppm | 2.33 to 3.0 ppm |
| hydrogen of —CH—CN | 6.33 ppm | 6.37 ppm |
| ethylene hydrogens | 6.65 to 6.7 ppm | 6.63 to 6.77 ppm |
| aromatic hydrogens | 6.88 to 7.43 ppm | 6.86 to 7.4 ppm |

Circular dichroism:

| isomer R | isomer S |
|---|---|
| Max ≦ 230 nm Δε = −9 | max towards 225 nm Δε = +11 |
| Max 268 nm Δε = −0.4 | max 285 nm |
| Max 280 nm Δε = −0.45 | Δε = +0.4 |

STEP F: 1R-[1α(R), 2α]4-[3-(cyano-[3-(2,2-dibromoethenyl)-2,2-dimethyl-cyclopropylcarbonyloxy]-methyl)-phenoxy]-benzene propanoic acid A mixture of 1.1 g of tertbutyl ester of isomer R of Step E and 55 ml of toluene was refluxed and 0.19 g of p-toluene sulfonic acid was added. After maintaining reflux for 30 minutes, cooling and filtering, the filtrate was evaporated to dryness under reduced pressure and the residue was chromatographed over silica. Elution with a mixture of hexane and ethyl acetate (1/1) obtained 0.93 g of 1R-[1α (R), 2α]4-[3-(cyano-[3-(2,2-dibromoethenyl)-2,2-dimethylcyclopropylcarbonyloxy]-methyl)-phenoxy]-benzene propanoic acid.

IR Spectrum (chloroform):

| 1,742 cm$^{-1}$ | $\overset{\text{O}}{\underset{\|}{\text{C}}}$ ester |
|---|---|
| 1,604 cm$^{-1}$<br>1,591 cm$^{-1}$<br>1,509 cm$^{-1}$<br>1,487 cm$^{-1}$ | aromatics |
| 1,712 cm$^{-1}$ | $\overset{\text{O}}{\underset{\|}{\text{C}}}$ dimer acid |

NMR Spectrum (CDCl$_3$)

| hydrogens of paired methyls and of tBu | 1.3 ppm |
|---|---|
| hydrogens of cyclopropyl (cis) | 1.8 to 2.19 ppm |
| hydrogens of CH$_2$ of the alkyl chain | 2.5 to 3.17 ppm |
| hydrogen of —CH—CN | 6.23 ppm |
| ethylene hydrogen | 6.6 to 6.73 ppm |
| aromatic hydrogens | 6.88 to 7.43 ppm |

EXAMPLE 2

1R-[1α(S), 2α]4-[3-(cyano-[3-(2,2-dibromoethenyl)-2,2-dimethyl-cyclopropylcarbonyloxy]-methyl)-phenoxy]-benzene propanoic acid A mixture of 1.805 g of the tertbutyl ester (S) obtained in Example 1 and 90.25 ml of toluene was refluxed and 0.18 g of p-toluene sulfonic acid was added. Reflux was maintained for 30 minutes and after cooling, filtering and evaporation to dryness under reduced pressure, the residue was chromatographed over silica and eluted with a mixture of hexane and ethyl acetate (1/1) to obtain 1.33 g of 1R-[1α(S), 2α]4-[3-(cyano-[3-(2,2-dibromoethenyl)-2,2-dimethylcyclopropylcarbonyloxy]-methyl)-benzene propanoic acid.

IR Spectrum (chloroform).

| 1,742 cm$^{-1}$ | $\overset{\text{O}}{\underset{\|}{\text{C}}}$ ester |
|---|---|
| 1,604 cm$^{-1}$<br>1,591 cm$^{-1}$<br>1,509 cm$^{-1}$<br>1,487 cm$^{-1}$ | aromatics |
| 1,712 cm$^{-1}$ | $\overset{\text{O}}{\underset{\|}{\text{C}}}$ dimer acid |

NMR Spectrum (CDCl$_3$)

| hydrogens of paired methyls: | 1.2 to 1.25 ppm |
|---|---|
| hydrogens of cyclopropyl: | 1.82 to 2.23 ppm |
| hydrogens of CH$_2$ of the alkyl chain | 2.5 to 3.17 ppm |
| hydrogen of —CH—CN | 6.43 ppm |
| ethylene hydrogen | 6.68 to 7.16 ppm |
| aromatic hydrogens | 6.97 to 7.7 ppm |

EXAMPLE 3

1R-[1α(S), 2α]4-[3-(cyano-[3-(2,2-dibromoethenyl)-2,2-dimethyl-cyclopropylcarbonyloxy]-methyl)-phenoxy]-benzene-N-[2,2-iodo$^{125}$I 4-1H-imidazolyl)-ethyl]-propanamide

STEP A: Preparation of mixed anhydride in solution (solution A)

25 μl of anhydrous dioxane were mixed under argon with 10 μl of tri-n-butylamine diluted to 1/125 in anhydrous dioxane and 10 μl of isobutyl chloroformate diluted to 1/250 in anhydrous dioxane and a solution of 150 g of 1R-[1α(S), 2α]4-[3-(cyano-[3-(2,2-dibromoethenyl)-2,2-dimethylcyclopropylcarbonyloxy]-methyl)-phenoxy]-benzenepropanoic acid in 25 μl of anhydrous dioxane was added. The mixture was maintained for 30 minutes at 20° C. with stirring and the reaction mixture was diluted with 125 μl of anhydrous dioxane to obtain solution A of mixed anhydride.

STEP B: Marking the histamine

10 μl of 2 mM of histamine base solution in a 0.5M sodium phosphate buffer at pH 7.4, 1 m Ci of $^{125}$INa and 10 μl of a 5 mg/ml aqueous solution of chloramine T were mixed together at 20° C. and after 90 seconds, 10 μl of a 25 mg/ml aqueous solution of sodium metabisulfite were added to obtain medium B which was checked by chromatography. (see FIG. 2)

STEP C: Condensation

50 μl of solution A of mixed anhydride were introduced into the tube containing the reaction medium B and the mixture was held at 4° C. for 2 hours to obtain solution C which was analyzed by chromatography (see FIG. 3).

STEP D: Purification

The reaction medium C was purified by HPLC on a Zorbax Golden Sil column, 100×7.5 nm, 3 μm, eluted with a chloroform-methanol mixture (92/8). The radioactivity of the effluent was followed by a Beckman 170 sodium iodide crystal detector coupled to an integrating recorder. 4 peaks were obtained (see Table I) and only peak 3 contained an antigen which was linked to an "antideltamethrin" antibody. The fractions containing the immunoreactive product were combined to obtain solution D (FIG. 4). The mixture was evaporated to dryness under argon and 5 ml of ethanol were added to the residue to obtain about 600 μCi or radioactive conjugate. The product, stored at −30° C., was stable for at least 2 months.

EXAMPLE 4

1R-[1α(R), 2α]4-[3-(cyano-[3-(2,2-dibromoethenyl)-2,2-dimethylcyclopropylcarbonyloxy]-methyl)-phenoxy]-benzene-N-[2-(2-iodo$^{125}$I 4-1H-imidazolyl)-ethyl]-propanamide

STEP A: Preparation of the mixed anhydride in solution (solution A)

25 μl of anhydrous dioxane, 10 μl of tri-n-butyl amine diluted to 1/125 in anhydrous dioxane and 10 μl of isobutyl chloroformate diluted to 1/250 in anhydrous dioxane were mixed under argon and 150 μg of 1R-[1α(R), 2α]4-[3-(cyano-[3-(2,2-dibromoethenyl)-2,2-dimethylcyclopropylcarbonyloxy]-methyl)-phenoxy]-benzene propanoic acid in solution in 25 μl of anhydrous dioxane were added. The mixture was held at 20° C. for 30 minutes and the reaction mixture was diluted by 125 μl of anhydrous dioxane to obtain solution A of mixed anhydride.

STEP B: Marking the histamine

10 μl of 2 mM histamine base solution in a 0.5M sodium phosphate buffer at pH 7.4 was mixed at 20° C. with 1 m Ci of $^{125}$I Na and 10 μl of a 5 mg/ml aqueous solution of chloramine T and after 90 seconds, 10 μl of a 25 mg/ml aqueous solution of sodium metabisulfite were added to obtain medium B which was checked by chromatography. (See FIG. 6).

STEP C: Condensation

50 μl of solution A of mixed anhydride were introduced into the tube containing reaction medium B and the mixture was held at 4° C. for 2 hours to obtain the solution C which was analyzed by chromatography (see FIG. 7).

STEP D: Purification

The reaction medium C was purified by HPLC on a Zorbax Golden Sil column, 100×7.5 nm, 3 μm, eluted by a chloroform-methanol mixture (97/3). The radioactivity of the effluent was followed by a Berthold sodium iodide crystal detector and 4 peaks were obtained (see FIG. 5). Only peak 3 contained an antigen capable of being linked to "antideltamethrin" antibodies. The solution D (FIG. 8) obtained was evaporated to dryness under argon and 5 ml of ethanol were added to the residue. 220 μCi of radio active conjugate were obtained and the product stored, at −30° C., was stable for at least 2 months.

EXAMPLE 5

Conjugate of bovine serum albumin and 1R-[1α(S), 2α]4-[3-(cyano-[3-(2,2-dibromoethenyl)-2,2-dimethylcyclopropyl-carbonyloxy]-methyl)phenoxy]-benzene propanoic acid

STEP A: Preparation of the mixed anhydride 115.5 mg of 1R-[1α(S), 2α]4-[3-(cyano-[3-(2,2-dibromoethenyl)-2,2-dimethylcyclopropylcarbonyloxy]-methyl)-phenoxy]-benzene-propanoic acid were mixed with 2 ml of anhydrous dioxane and a mixture of 47 μl of tri-n-butyl amine and of 27 μl of isobutyl chloroformate were added. The resulting mixture was stirred for 30 minutes at 13° C.

STEP B: Preparation of the BSA solution

A mixture of 8 ml of water, 276 mg of BSA and 800 μl of dioxane was stirred for 20 minutes at +4° C. 18 ml of dioxane were added and the formation of a white, milky precipitate was observed which disappeared with the addition of 100 μl of an N aqueous solution of sodium hydroxide whereby the pH of the solution was adjusted to 7.9 to 8.0.

STEP C: Condensation

The mixed anhydride solution was slowly added at +4° C. to the BSA solution whereby the formation of a milky precipitate was observed. The pH fell from 8.0 to 7.4 at which value it was maintained for 5 hours of agitation at +4° C.

STEP D: Purification

The milky solution obtained was dialyzed in a Visking apparatus 36/32 of 20×3 cm against 6 times 5 liters of water. The residue obtained was lyophilized for 48 hours in an Usilfroid SMH 015 apparatus to obtain 311 mg of a white solid.

Analysis:
% Br 8.7;
% N 11.9.

UV Spectrum, circular dichroism: chromophore

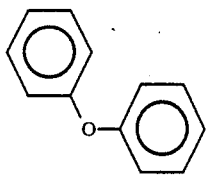

absorbing in the same region as the BSA which makes the determination inaccurate. Estimation: $6.10^{-5}$ mole/g of product.

EXAMPLE 6

Conjugate of bovine serum albumnin and 1R-[1-α(R), 2-α]4-[3-(cyano-[3-(2,2-dibromoethyl)-2,2-dimethylcyclopropylcarbonyloxy methyl) phenoxybenzene propanoic acid

STEP A: Preparation of the mixed anhydride

A mixture of 115.5 mg of 1R-[1α(R), 2α]4-[3-(3,2-dibromoethenyl)-2,2-dimethylcyclopropylcarbonyloxy]-methyl)]phenoxy]-benzene-propanoic acid and 2 ml of anhydrous dioxane was mixed with a mixture of 47 μl of tri-n-butylamine and of 27 μl of isobutyl chloroformate and the resulting mixture was stirred for 30 minutes at 15° C.

STEP B: Preparation of the BSA solution

A mixture of 8 ml of water, 276 mg of BSA and 800 μl of dioxane was stirred for 20 minutes at +4° C. and 18 ml of dioxane were added. The formation of a white, milky precipitate was observed which disappeared with the addition of 50 μl of N aqueous solution of sodium hydroxide whereby the pH of the solution was adjusted to 7.9 to 8.0.

STEP C: Condensation

The solution of mixed anhydride was slowly added at +4° C. the BSA solution whereby a milky precipitate was formed whereby the pH fell from 8.0 to 7.5, at which value it was maintained for 5 hours with stirring at +4° C.

STEP D: Purification

The milky solution obtained was dialyzed in a Visking apparatus 36/32 of 3×15 cm, against 12 times 5 liters of water to obtain a suspension which was lyophilized for 48 hours in an Usifroid SMH 015 apparatus.

Analysis:
% Br 9.5;
% N 11.5.

Various modifications of the products and methods of the invention may be made without departing from the spirit or scope thereof and it is to be understood that the invention is intended to be limited only as defined in the appended claims.

What we claim is:

1. The optical isomers and racemic mixtures of novel radioactive pyrethrinoids marked with iodine of the formula

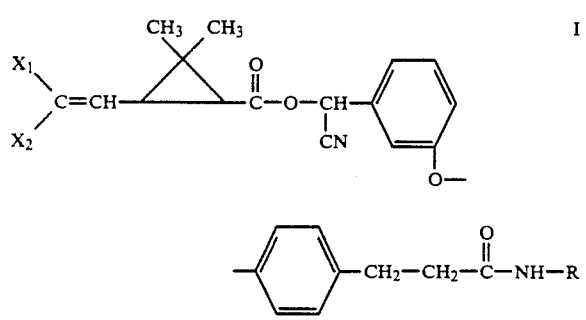

wherein $X_1$ is selected from the group consisting of halogen and —$CF_3$, $X_2$ is a halogen, RNH is the residue of a member selected from the group consisting of histidine, tyrosine, histidinol, histamine, tyramine and methyl tyrosinate marked with iodine$^{125}$ or iodine$^{131}$.

2. A compound of claim 1 wherein $X_1$ is selected from the group consisting of —$CF_3$, chlorine and bromine and $X_2$ is chlorine or bromine.

3. A compound of claim 1 wherein $X_1$ and $X_2$ are bromine.

4. A compound of claim 1 which is 1R-[1α(S), 2α-]4-[3-(cyano-[3-(2,2-dibromoethenyl)-2,2-dimethylcyclopropylcarbonyloxy]-methyl)-phenoxy]-benzene-N-[2-(2-iodo$^{125}$I 4-1H-imidazolyl)-ethyl]-propanamide of the formula

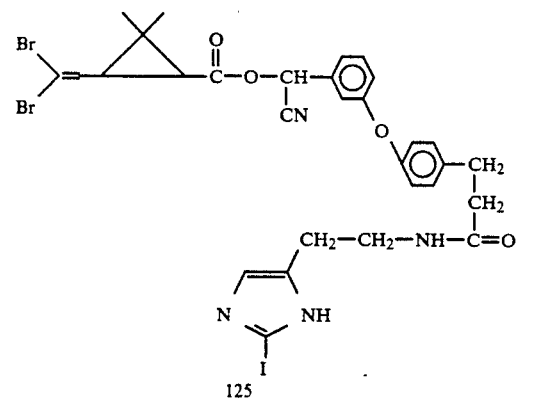

5. In a process for the radioimmunological determination of pyrethrinoid esters of α-cyano-3-phenoxy-benzyl alcohol in biological fluids of man and warm-blooded animals, the improvement comprising using a compound of claim 1 of the pyrethrin as the said ester as reagent.

6. The process of claim 5 wherein the reagent is 1R-[1α(S), 2α-]4-[3-(cyano-[3-(2,2-dibromoethenyl)-2,2-dimethylcyclopropylcarbonyloxy]-methyl)-phenoxy]-benzene-N-[2-(2-iodo$^{125}$I 4-1H-imidazolyl)-ethyl]-propanamide of the formula

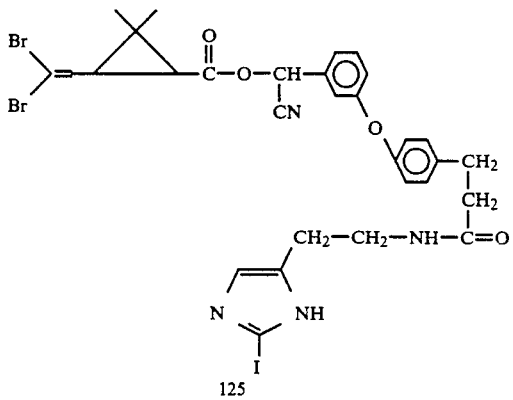

7. An antigen formed by conjugating through the carboxyl group a compound of the formula

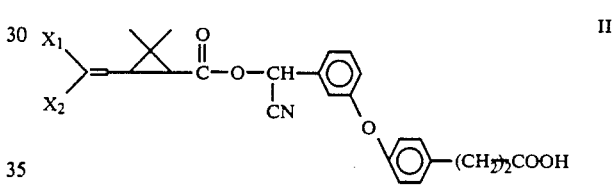

with and immunogenic protein wherein $X_2$ is halogen and $X_1$ is halogen or —$CF_3$.

8. An antigen of claim 7 wherein the immunogenic protein is bovine serum albumin.

9. An antigen of claim 7 with the formula selected from the group consisting of

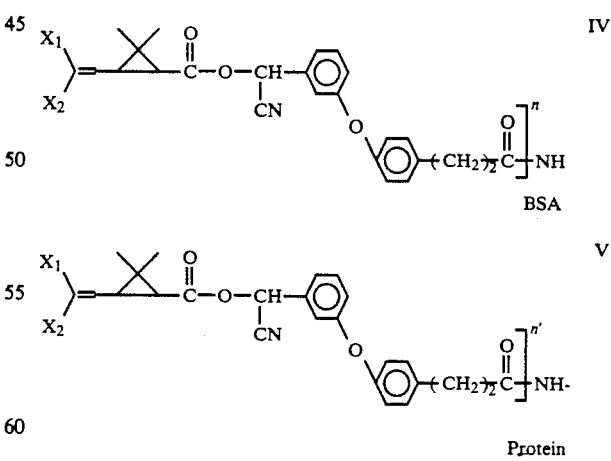

wherein n is an integer from 10 to 30, n' is an integer from 10 to 100 and $X_1$ is selected from the group consisting of —$CF_3$ and halogen and $X_2$ is halogen.

10. In the preparation of antibodies, the improvement comprising using an antigen of claim 7.

* * * * *